United States Patent
Schlaeppi

(10) Patent No.: US 6,187,986 B1
(45) Date of Patent: Feb. 13, 2001

(54) FRESH PLANT INVENTORY HYDROFLUORIC ACID EDUCTION PROCESS

(75) Inventor: Dan R. Schlaeppi, Robinson, IL (US)

(73) Assignee: Marathon Ashland Petroleum, LLC, Findlay, OH (US)

( * ) Notice: Under 35 U.S.C. 154(b), the term of this patent shall be extended for 0 days.

(21) Appl. No.: 09/411,128

(22) Filed: Oct. 4, 1999

Related U.S. Application Data

(60) Provisional application No. 60/103,409, filed on Oct. 17, 1998.

(51) Int. Cl.$^7$ ................................. C07C 2/58; C07C 2/60
(52) U.S. Cl. ........................... 585/723; 585/710; 585/720
(58) Field of Search ..................... 585/710, 720, 585/723

(56) References Cited

U.S. PATENT DOCUMENTS

| | | |
|---|---|---|
| 2,894,999 | 7/1959 | Lawson . |
| 3,551,515 * | 12/1970 | Gentry ................................. 585/706 |
| 3,910,771 | 10/1975 | Chapman . |
| 3,919,342 * | 11/1975 | Chapman ............................ 585/703 |
| 4,014,953 | 3/1977 | Brown, Jr. . |
| 4,046,516 | 9/1977 | Burton et al. . |
| 4,199,409 | 4/1980 | Skraba . |
| 4,236,036 * | 11/1980 | Dixon et al. ......................... 585/331 |
| 4,239,931 | 12/1980 | Mikulicz . |
| 4,276,257 * | 6/1981 | Dixon et al. ............................ 422/62 |
| 4,982,036 | 1/1991 | Hachmuth et al. . |
| 5,185,487 | 2/1993 | Love et al. . |
| 5,220,094 * | 6/1993 | Eason .................................. 585/716 |
| 5,304,522 | 4/1994 | Jalkian et al. . |
| 5,322,673 | 6/1994 | Eason . |
| 5,334,788 | 8/1994 | Baucom et al. . |

* cited by examiner

*Primary Examiner*—Walter D. Griffin
(74) *Attorney, Agent, or Firm*—Richard D. Stone

(57) ABSTRACT

A slipstream of high pressure, cooled isobutane recycle from within an alkylation process unit is used to withdraw hydrofluoric acid from a storage vessel by means of an eductor and discharges the same into a reactor section of the unit. The eductor is preferably constructed of HASTELLOY "C" which provides both corrosion resistance to HF acid and has excellent surface hardness to withstand the highly erosive eductor application. This eductor eliminates potential release of HF acid due to failure of conventional rotating equipment seals or sealing systems, is low cost, has no moving parts, and is fireproof (will not lose containment during a fire).

13 Claims, 2 Drawing Sheets

FRESH PLANT INVENTORY HYDROFLUORIC ACID EDUCTION PROCESS

This application claims the benefit of U.S. Provisinal Application No. 60/103,409, filed Oct. 17, 1998.

FIELD OF THE INVENTION

The present invention relates to the art of catalytic alkylation. More specifically, the invention relates to a method for adding fresh or inventoried liquid alkylation catalyst, to an alkylation unit.

BACKGROUND OF THE INVENTION

Alkylation is a reaction in which an alkyl group is added to an organic molecule. For example, an isoparaffin can be reacted with an olefin to provide an isoparaffin of higher molecular weight. In petroleum refining, the process reacts a $C_2$ to $C_5$ olefin with isobutane in the presence of an acidic catalyst to produce an upgraded product stream referred to as alkylate. This alkylate is a valuable blending component in the manufacture of gasoline due not only to its high octane rating but because it is free of aromatic components.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of petroleum Refining Processes* 23–28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry uses anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

In addition to these efforts directed at making the HF acid circulating in a plant safer by reducing its cloud forming tendencies, there is concern about making every part of the process safer. One significant hazard, which has previously been overlooked by others, is adding fresh HF acid to the plant. A similar problem is re-inventory, that is, the return of the HF acid inventory to the plant after a plant shutdown to permit repair or inspection of equipment.

Now this is done by rotating equipment, typically pumps with seals. Such equipment can and does leak or fail. Standard practice is to use tandem seals which should prevent a catastrophic leak, however failures do happen and leaks can occur.

Usually the fresh acid, added to replenish acid consumed or lost during processing, is relatively pure acid. Fresh acid does not contain sulfolane or other agents which are present in the HF acid circulating in acid inventory of the plant, so it represents a potential threat to the environment even when sulfolane or the like is present in the acid inventory.

Some efforts have been made to reduce the amount of rotating pumps used in HF alkylation units, which are reviewed briefly hereafter.

TRANSFER OF HF ACID WITHIN AN ALKYLATION PLANT

U.S. Pat. No. 5,334,788, Baucom et al, taught fluorine gas reactions in an eductor.

U.S. Pat. No. 5,322,673, a Division of U.S. Pat. No. 5,220,094 taught use of an alkylation recontactor with an internal mixer. FIG. 2 showed an eductor moving acid inventory and mixing it with hydrocarbon.

U.S. Pat. No. 5,304,522, Jalkian et al, taught use of an eductor to process a slurry of solid sorbent with an alkylate rich stream and a sulfolane-enriched stream, which had previously been stripped of most HF acid in an HF stripper. The sulfolane was added as a vapor suppressant, but the process is still basically an HF alkylation unit with an acid inventory less likely to form a large vapor cloud if accidentally released.

U.S. Pat. No. 5,185,487, Love et al, taught use of an eductor to mix organic fluoride-containing alkylate with HF acid to release the HF and make more alkylate.

U.S. Pat. No. 4,349,931, Mikulicz, taught use of eduction to move an HF containing stream from a reactor to a stripping column. The hydrocarbon stream used as a "pumping means, comprises about 92 mole % isobutane, 2 mole % propane and 6 mole % n-butane."

U.S. Pat. No. 4,199,409, Skraba, taught use of an eductor to recycle an HF rich acid soluble oil (ASO) from the bottoms to various intermediate levels of an HF acid rerun column. The motive fluid was isobutane vapor.

U.S. Pat. No. 4,046,516 Burton et al, taught use of an eductor to transfer catalyst from one reaction zone in the HF alkylation unit to another.

U.S. Pat. No. 4,014,953, Brown taught use of an eductor in the base of the acid regenerator associated with an HF alkylation unit. Isoparaffin was the drive fluid, and stripping fluid, for a liquid ASO stream containing HF.

U.S. Pat. No. 3,910,771, Chapman, taught use of something similar to an eductor in a vessel designed to convert alkyl fluorides in HF alkylate into alkylate.

U.S. Pat. No. 2,894,999, Lawson, taught use of an eductor in an HF alkylation plant, using relatively hot, high pressure vapor from the deisobutanzier to educt vapor from, and provide evaporative cooling of, an HF alkylation reactor.

These patents were directed to "internal" eductors, that is, eductors moving an HF containing liquid from one place in the relatively high pressure HF alkylation plant to another place within the plant. The relatively modest pressure differentials, and the fact that the liquid streams being educted were under relatively high pressure made eductors safe and easy to use.

FRESH ACID TRANSFER

Despite the widespread use of eductors for internal liquid transfer in HF units, they have never been used, so far as is known, to add either fresh or inventoried HF acid back into the unit. Acid eggs have probably been used. One approach, reviewed below, avoided mechanical equipment, but called for a sophisticated device with a significant number of extra valves and pressure gages, all potential "weak spots" in an HF alkylation plant.

U.S. Pat. No. 4,982,036, Hachmuth et al, taught use of compressed gas to transfer acid catalyst from a transport vehicle to the alkylation process. The approach is similar to use of an "acid egg", wherein acid is added to a vessel, following which the vessel is pressurized with a gas to provide the "head" needed to transfer the acid to the desired location. While a useful approach, it involves some capital expense for vessels and creates volumes of inert gas—the drive fluid used to energize the "acid egg"—which must eventually be processed.

Thus while many improvements have been made in the HF alkylation process, such as the above mentioned attempts to reduce the use of mechanical pumps in the process, there were still some problems.

One problem area was getting fresh acid into the plant to periodically make up for acid losses. Now mechanical pumps are used to do this and these can leak or fail. Use of a pump with shut off valves at a remote tank leaves a significant amount of concentrated HF acid in the pump and the transfer line to the plant. While concentrated HF acid is not especially corrosive, there are concerns about having any inventory of this material around to leak out if a flange gasket leaks or valve stem packing fails. To overcome this problem, refiners provide flush lines to permit displacement of HF acid into the plant. This safely removes the acid in the pump and transfer line, but introduces additional valves and lines.

The problems are exacerbated because fresh acid is typically added only once a week or once a month, as determined by the needs of the plant for fresh acid addition to maintain acid strength. Pumps which are used continuously are more reliable than those which run for only a few hours once a week or once a month. The seals are especially troublesome, and such pumps typically use dual seals, and flush the seals with isobutane so that the pumps "see" as little HF as possible, but even with these precautions, seals fail. The use of isobutane flush liquid at least makes it relatively easy to spot a failed seal in that isobutane vaporizes and the cooling due to "autorefrigeration" causes condensation/frost buildup on the pump.

Another problem with conventional approaches to acid replenishmnent is that the plant is frequently "shocked" by the addition of large amounts of fresh acid. The sudden increase in acid concentration in the mixer settler causes an alkylate production spike which causes a minor unit upset until the fresh acid is diluted and the alkylate production returns to normal. While this could theoretically be avoided by adding the makeup acid at a lower rate, or at more frequent intervals, in practice plant operators want to add acid quickly and be done with it. Additional upset occurs because 2,000 to 5,000 gallons of fresh, liquid HF acid is added to the plant. This liquid volume physically displaces hydrocarbon rich liquid from the settler, leading to a sudden apparent increase in alkylate production.

More frequent addition, e.g., daily or hourly addition is not advisable for safety reasons. It is best not to operate acid addition pumps any more often than is necessary so turning pumps repeatedly on and off is not recommended. Slower addition is not an option in many plants as the pumps are sized relatively large to handle multiple jobs. An additional concern is that centrifugal pumps rely on fluid flow for cooling of the pump. The pump, and or the driver, can be damaged if the pump is started with the discharge line fully closed or even partially open without adequate fluid flow.

Use of an "acid egg" to transfer fresh acid is theoretically possible, but requires significant capital expense to provide the "egg" to hold the acid and a relatively complicated and expensive manifold system to provide pressurizing gas. Great care must be taken to isolate the "egg" from the fresh HF acid storage tank, lest the storage tank be overpressured causing tank failure or large discharge of vapor through the tank's relief valve or rupture disk. Relatively high pressures would be required, typically around 300 psig, to move relatively large amounts of fresh HF acid through a system of transfer lines into an HF alkylation unit operating at relatively high pressures, typically 200–300 psig. Additional precautions would need to be taken to prevent, or deal with, possible discharge of large amounts of pressuring gas into the HF alkylation unit.

Thus while the "acid egg" approach would permit acid addition without a mechanical pump, the cost of multiple valves and an extra high pressure rated vessel costs, by my estimate, about two to four times the cost of a mechanical pump. I was also concerned about all the additional possible acid leak points, maintenance of such a system and possibly lower reliability.

A related but less severe problem is restarting after a shutdown. During a complete shutdown, to permit an inspection or work on the unit, the entire acid inventory of the plant is removed and sent to a secure HF acid inventory storage drum. During startup, the procedure is reversed. This involves transfer of the acid inventory from the HF acid inventory storage drum back into the HF alkylation unit. Such a transfer usually occurs only after a unit shutdown when there is less concern about upsetting the unit.

The difficulty of restoring the acid inventory is similar to that of adding fresh HF acid to the operating plant. The plant during startup runs at essentially the same pressure in the reactor section as during normal operation and the pressure in the acid inventory tank is essentially the same as the pressure in the fresh HF acid storage tank.

The amount of HF acid in inventory may be similar to or much larger than the amount of fresh HF acid added to replenish losses, but inventory replacement is infrequent while acid replenishment occurs frequently.

Some plants use the same vessel for acid inventory and HF addition, some use separate vessels. Most HF units use one relatively large, dedicated, infrequently used pump to restore acid inventory after a shutdown and a separate, dedicated, smaller and more frequently used pump to add fresh acid.

A high capacity pump is used to restore inventory because rapid addition of acid inventory, after a plant shutdown, minimizes downtime. The plant is not going to be "upset" by rapid restoration of acid after a shutdown, so operators do not need to be slow in restoring acid inventory. Slow addition of fresh, or makeup, acid, is desired to minimize plant upsets dues to changes in catalytic production of alkylate or physical displacement of alkylate, so a smaller pump is used for fresh acid addition than is used to restore plant inventory after a shutdown.

I wanted to eliminate as much rotating mechanical equipment as possible from the HF alkylation unit, to reduce possible harm to the environment and to eliminate the cost of maintaining this mechanical equipment. I also wanted to reduce the amount of HF acid that was in relatively exposed and vulnerable process lines, which can be broken if equipment is dropped on them, or vehicles driven into them.

I also wanted to reduce or eliminate the unit upsets which now occur when a large slug of fresh HF acid is added to the unit to make up acid consumed in the process. I wanted to be able to reinventory the plant, after a shutdown.

I found that eductors, and special operating procedures, could be used to eliminate much mechanical equipment in an HF alkylation unit and eliminate unit upsets when fresh acid is added.

BRIEF SUMMARY OF THE INVENTION

Accordingly, the present invention provides a HF alkylation process comprising mixing liquid HF acid, a fresh isobutane feed stream, a recycle isobutane stream and a fresh olefin feed stream to form a liquid mixture; alkylating said olefins in said mixture with isobutane in an HF alkylation reactor operating at HF alkylation conditions including a pressure sufficiently high to maintain said isobutane in the liquid phase in at least a portion of said reactor, to form a liquid mixture comprising isoparaffinic alkylate produced in the course of said alkylation reaction, alkyl fluorides, and HF contaminated with a minor amount of acid soluble oil (ASO) produced during said alkylation reaction; separating said mixture into an alkylate product rich phase, a recycle HF acid phase, and an isobutane recycle phase; regenerating, at least periodically, a portion of said liquid HF acid in an acid regenerator to remove ASO therefrom and produce an ASO stream containing a minor portion of acid or alkyl fluorides and a regenerated HF acid stream which is recycled to said alkylation reactor; consuming, at least a portion of said liquid HF acid by at least one of mechanical loss, formation of alkyl fluorides which remain in a liquid alkylate product phase, or losses associated with a regeneration step; storing fresh HF acid in an HF acid storage vessel at liquid HF storage conditions sufficient to maintain said acid in a liquid phase and at a superatmospheric pressure which is below the pressure of said alkylation reactor; educting, at least periodically, liquid HF acid from said storage vessel to said HF alkylation process by educting liquid HF acid from said storage vessel using an eductor and as a motive fluid a liquid phase hydrocarbon feed or product stream associated with said alkylation process.

In another embodiment, the present invention provides a method of periodically adding fresh or makeup HF acid to an HF alkylation process operating at a pressure above 200 psig from a liquid HF acid storage tank operating at a pressure below 200 psig and wherein said pressure differential between said process and said storage tank is sufficient to preclude use of a recycle isobutane stream produced in said alkylation process to educt liquid HF from said storage tank into said alkylation process comprising temporarily increasing the pressure in said liquid HF storage tank above said normal storage tank operating pressure; diverting a portion of a recycle isobutane stream from said plant to use as a motive fluid in an eductor fluidly connected with said liquid HF storage tank; said alkylation reaction; discharging from said eductor a stream comprising isobutane motive fluid and educted liquid HF acid into a portion of said HF alkylation process.

In yet another embodiment the present invention provides a method of restoring an inventory of HF acid to an HF alkylation process after a shutdown of the HF alkylation plant to permit using said inventory of HF acid to alkylate a fresh olefin stream with a stream comprising recycle isobutane produced in one or more fractionators to produce alkylate comprising: restoring isobutane recycle by adding isobutane and a startup alkylate stream to said alkylation unit and fractionating same in said one or more fractionators to produce an isobutane recycle stream and a startup alkylate stream with a reduced isobutane content to establish temperatures and operating conditions in said one or more fractionators and startup pressures in said process; educting a stored HF inventory from an HF inventory storage tank operating at HF storage conditions including a pressure less than said startup pressure in said process into said HF alkylation plant using a recycle isobutane stream produced by said one or more fractionators to produce an HF alkylation plant with isobutane recycle established and an inventory of HF acid in the plant.

DETAILED DESCRIPTION OF PREFERRED EMBODIMENTS

The HF alkylation process is conventional, well known and widely used. Detailed discussion thereof, beyond that of the prior art patents previously reviewed, which are incorporated by reference, is not necessary.

Figure 1:
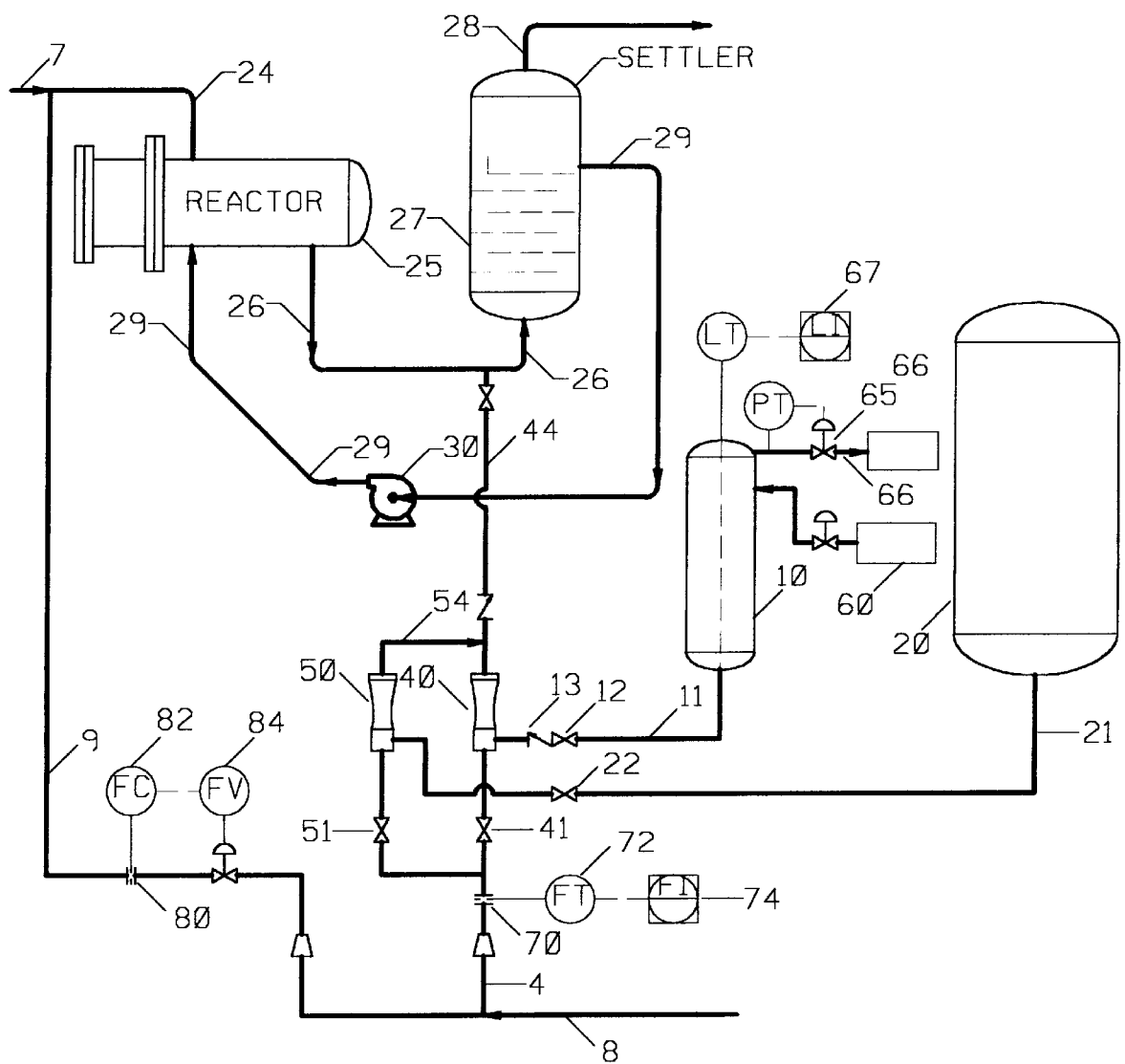
FIG. 1 is a simplified schematic diagram illustrating the major processing steps of one embodiment of the present invention, using dual eductors and separate storage drums for fresh and inventory acid.

FIG. 1 is a simplified, schematic flow diagram of a conventional HF alkylation unit, with many pumps, instrumentation and like equipment omitted for the sake of clarity. Light olefins in line 7 are mixed with an isobutane rich stream in line 9 and charged via line 24 to alkylation reactor 25. A liquid, HF rich acid phase is charged to the reactor via line 29.

An emulsion of HF acid, alkylate, and unreacted reactants is discharged from the reactor via line 26 and charged to settler 27. A liquid hydrocarbon phase containing the alkylate and light hydrocarbons is removed from an upper portion of the settler via line 28 for further processing in means not shown. Such processing recovers a high octane alkylate product fraction, which is a gasoline blending stock, and a recycle isobutane fraction which is returned to the process via line 8.

An acid phase is withdrawn from the settler via line 29 and recycled to the reactor via catalyst circulating pump 30 and line 29.

Acid is lost or consumed during the alkylation process and/or during the acid regeneration process (not shown) wherein acid soluble oil (ASO) is removed from the recirculating HF acid to maintain the purity thereof. To maintain an appropriate acid inventory and acid strength, at least periodically, and typically once every week or every other week, fresh HF acid is added to the unit from HF acid storage drum 10. Acid is stored in this vessel under a fuel gas blanketing system 60, with any gas vented via pressure controller 65 and line 66 to an acid flare. Drum 67 also includes a level indicating system 67, which shows the level of HF acid in the drum. It is not possible to use a conventional sight glass to determine the acid level because the HF acid would attack the glass.

In the process of the present invention, fresh HF acid is withdrawn from drum 67 via line 11, block valve 12 and check valve 13 and charged to eductor 40. The driving fluid for the eductor is preferably recycle isobutane which passes via lines 8 and 4 through flow indicator/controller 70 and shut off valve 41 to eductor 40. Relatively high pressure isobutane educts HF acid from the storage drum 10 into the acid settler via lines 44 and 26.

In the embodiment shown, it is also possible to re-inventory the plant after a shutdown. The acid inventory tank 20, which is much larger than drum 10, contains not fresh HF acid, but rather the slightly diluted HF acid inventory of the plant, diluted with acid soluble oil (ASO) and minor amounts of dissolved and/or entrained isobutane and alkylate, and a very small amount of water. The contents of this vessel is the suction fluid to eductor 50. Thus the acid inventory is educted back into the plant by passing via line 21 and valve 22 into eductor 50, which will usually be much larger than eductor 40. The motive fluid is preferably recycle isobutane, charged via lines 8 and 4 and valve 51 into eductor 50, with the educted fluid being discharged via lines 54 and 44 into line 26 to enter the settler 27.

Figure 2:
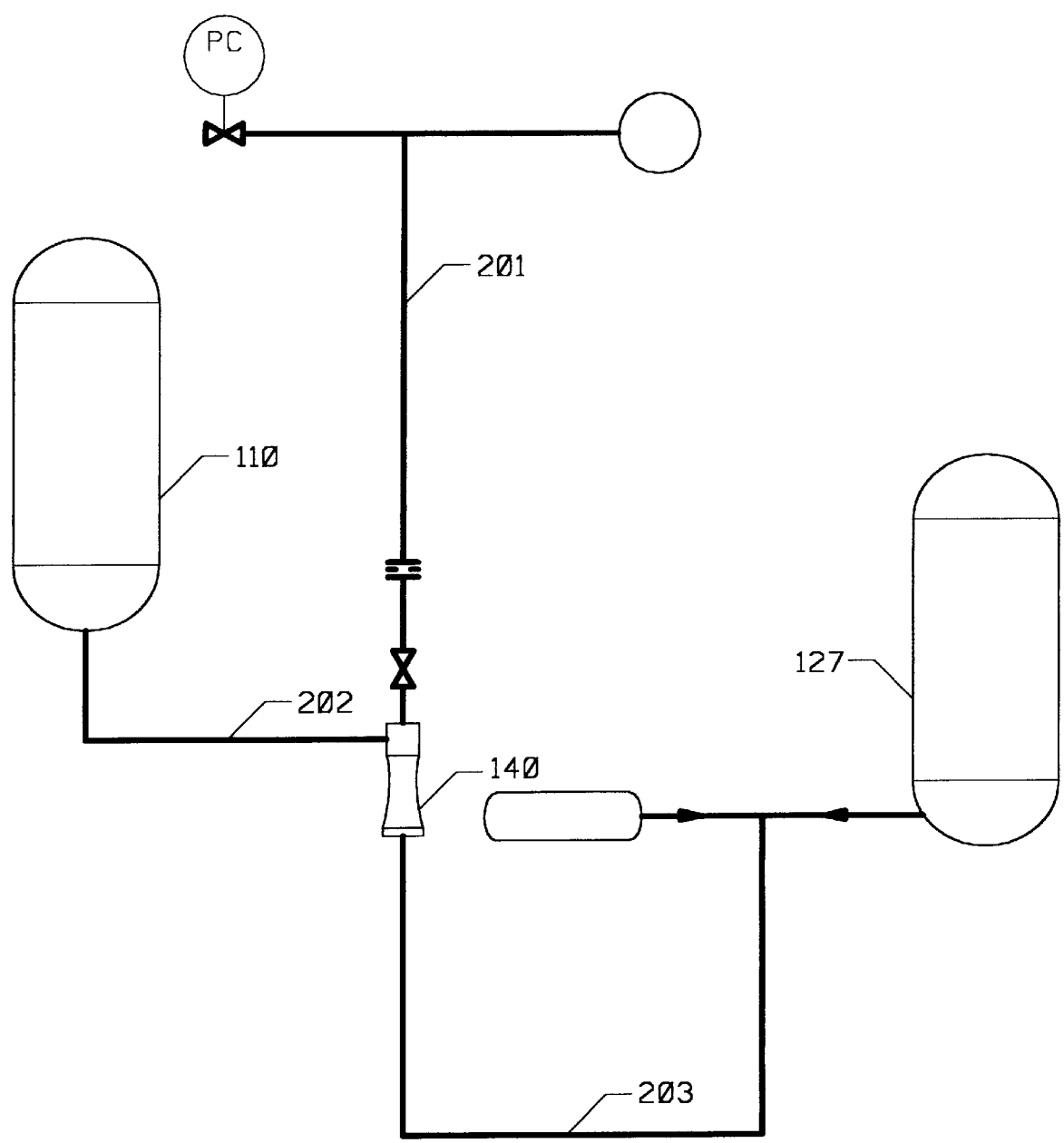
FIG. 2 is a simplified process flow of an embodiment using a single eductor and single storage drum for both fresh and inventory acid.

FIG. 2 shows a highly simplified process flow of the process. Acid (both fresh and, when needed, acid inventory) is stored in tank 110 and transferred via eductor 140 into settler 127 or other process vessel within the plant. Acid from tankage flows via line 202 to meet recycle isobutane in line 201, with the eductor effluent transferred via line 203 to vessel 127.

The operating conditions are changed somewhat depending on whether weekly fresh acid addition to maintain acid strength is practiced, flow condition 1, or if the plant is being rapidly re-inventoried after a shutdown, flow condition 2.

Fluid flows and fluid pressures during flow condition 1 can be summarized as follows: pressure at the base of vessel 110 will typically be 83 psig, with flowthrough line 202 being 25 gpm. Flowthrough line 201 will be 228 gpm and the pressure will be 315–319 psig. Pressure downstream of eductor 140 in line 203 will be 213 psig, with a flow of 253 gpm.

During flow condition 2 vessel 110 will have a bottom pressure of about 125 psig and flowthrough line 202 will be 150 gpm. Flowthrough line 201 will be 600 gpm and pressure just upstream of the eductor 140 will be 310 psig. Flowthrough line 203 will be 750 gpm, and pressure will be 230 psig.

The design shown permits the same lines to be used to supply motive fluid, cooled recycle isobutane in this instance, to both the fresh acid eductor and the acid inventory eductor.

The use of two eductors, or different sizes/capacities, and with each closely associated with the appropriate storage tank, makes it harder for an operator to inadvertently upset the unit by adding acid too quickly.

One benefit of using a modestly sized eductor to add fresh acid is the avoidance of minor plant upsets which will occur whenever a large volume of fresh acid is transferred into the mixer settler. A large amount of fresh acid increases acid purity/or physically displaced alkylate to produce an alkylate production spike. This caused a minor unit upset until the fresh acid was mixed in with the inventory and alkylate production returned to normal. Adding the fresh acid slowly significantly reduces this problem.

THE EDUCTION STEP

The eduction step involves an eductor, a motive fluid and a moved fluid (either fresh HF or the acid inventory of the plant. The theory, metallurgy, motive fluid and fluid moved, are reviewed at greater length below.

The design and use of eductors is well known. These are widely used in refineries in vacuum services and internally in HF alkylation units. The eductor uses a venturi principle. A high pressure motive fluid passes at relatively high velocity through the throat or narrow portion of a venturi to create a vacuum which draws a second fluid, called suction fluid, into the stream. The two fluids mix and are discharged from the eductor. The design of the venturi can be conventional and forms no part of the present invention.

The liquid/liquid eductor may be of any suitable configuration, and liquid/liquid eductors fabricated from nickel/copper alloys such as Monel brand alloys are preferred. For a discussion of liquid/liquid eductors, see generally R. H. Perry et al., 6 *Chemical Engineers' Handbook* 15 (5th ed., 1973). Eductors are generally taught in U.S. Pat. Nos. 4,815,942 to Alperin et al, 4,898,517 to Eriksen, and 4,960,364 to Tell, which patents are incorporated herein by reference.

In some applications the high strength HF acid can safely be handled by carbon steel. The composition or metallurgy of the eductor, per se, can be conventional and forms no part of the present invention. I prefer to use HASTELLOY"C" which provides both corrosion resistance to HF acid in all concentrations and has excellent surface hardness to withstand the highly erosive eductor environment.

For fresh HF acid addition, or to return the acid inventory to the plant after a shutdown, a motive fluid is essential. The motive fluid is preferably one which is compatible with the HF alkylation process, such as alkylate or isobutane. I prefer to use either recycle isobutane.

At first thought, it might seem obvious and easy to use isobutane, especially in view of its extensive use as a motive fluid for internal recycle within an HF alkylation plant. Isobutane is a well behaved liquid within the high pressure confines of the HF alkylation unit, which typically operates well above the vapor pressure of isobutane. On closer examination, refiners will learn isobutane is not suitable. Isobutane is a terrible motive fluid for moving a relatively low pressure material (HF acid in a storage tank) to a relative high pressure service (the high pressure environment within the HF alkylation plant).

When isobutane, or other high vapor pressure liquid material, is used, the liquid wants to assert its vapor pressure and will "vapor lock" the venturi. This vapor lock problem is not a problem within a conventional HF alkylation unit which operates at pressures of 200–300 psig, sufficiently high to keep isobutane in a liquid form.

Thus it is not possible to use isobutane as a motive fluid for HF acid when the HF acid is stored under conventional HF acid storage conditions and the HF has to be transferred into a plant operating at several 100 psi pressure. This is because the HF acid, for safety, is stored under relatively low pressure, usually 50 psig or less. Such pressures are enough to maintain the HF acid primarily in the liquid phase, but not sufficient to prevent vaporization of isobutane in the venturi where a small fraction of the liquid isobutane will vaporize, causing the venturi to "lose suction" and not be able to draw any HF acid into the venturi.

I devised a way, and specialized operating procedure, to permit use of isobutane, which was both safe and did not unduly increase production of HF contaminated tank vent gas. Modestly increasing pressure in the acid storage drum over the pressure level normally used for acid storage, preferably while temporarily resetting the vent pressure control system, was the key. Thus for a typical acid storage vessel operating at a pressure ranging from super-atmospheric to 50 psig, and typically from 20–40 psig, the pressure might be increased 10–50 psi, and/or the eductor located at an elevation sufficiently below that of the storage tank so that isobutane motive fluid will remain essentially liquid rather than vaporize.

Permanently, or temporarily, resetting the vent pressure control on the acid storage drum to some arbitrary pressure above the desired operating pressure of the tank, but well below the design pressure limit of the vessel, minimizes venting off the acid storage drum to the acid flare. This maximizes the amount of HF acid which is added to the plant and minimizes acid discharge to, and the impact on, the relief gas scrubbing system.

CONTROL OF ISORECYCLE

Use of relatively large amounts of isobutane as the motive fluid can present problems and opportunities. It is possible to use the existing isobutane recycle pumps, to supply isobutane as motive fluid for the eductor and recycle isobutane to the reactor. This eliminates the need to buy an additional pump (for isobutane motive fluid). The isobutane recycle pumps associated with an HF alkylation unit usually have some excess capacity, and in any event the pressure drop associated with getting isobutane through the eductor and into the acid settler (the preferred place to add fresh acid) is usually less than the pressure drop associated with getting isobutane through the reactor and into the settler.

I prefer to monitor, directly or indirectly, the amount of isobutane recycle to the reactor and reduce this in an amount roughly equivalent to the amount of isobutane motive fluid. This minimizes plant upsets which can, and do, occur when a large amount of fresh acid is suddenly added to the acid settler, and the minor upset due to reducing the iso:olefin ratio in the reactor. To accomplish this, flow indicator controllers on both the normal isobutane recycle line and on the motive fluid line may be used. A less accurate, and less effective, measure of control may be achieved by using an isobutane recycle pump of known characteristics and calculating the pressure drops associated with each isobutane line (recycle to the reactor and motive fluid). Measuring and/or controlling one fluid flow can be used to measure/control the other.

A additional benefit to using an alkylation plant hydrocarbon stream, preferably isobutane, as the motive fluid is that flushing of the eductor and lines is easy. After the desired amount of acid is added, flow of, e.g., isobutane through the eductor will purge the line of HF. It is beneficial, for safety and for corrosion, to reduce the amount of HF acid which is in lines. This can theoretically be achieved to some extent even when using reciprocating or centrifugal pumps, but increases the cost and complexity of the system. The only way to thoroughly purge a mechanical pump is to run the pump with a significant amount of the purge fluid flowing through the pump, and this would require fairly large isobutane flow lines.

General Guidelines for Plant Operators

Revise the operating procedures to operate the fuel gas regulator to the acid storage drum at 80 PSIG. This is necessary to make sure the eductor picks up suction on the isobutane flush in the lines at start up.

Revise the operating procedures to reset the vent pressure control on the acid storage drum to 135 PSIG. This will minimize venting off the acid storage drum to the acid flare which will retain additional HF Acid in the drum, and limit the impact on the relief gas scrubbing system.

EXAMPLE

The HF alkylation fresh acid eductor was commissioned and utilized to pump fresh acid from the HF acid storage drum to the mixer settler using isobutane as the motive fluid.

At 10:00 A.M. the eductor was lined out following the original operating guidelines. The isorecycle rate was lowered by 5,000 BPD to allow for operation of the eductor. The original operating procedures were to operate the eductor with a suction pressure of 50 PSIG. At this pressure, the eductor was not able to take suction. This was due to the suction line being filled with isobutane flush, and not HF acid. The decision was made by the unit foreman to raise the suction pressure to the eductor in order to force it to take suction. When the suction pressure was raised to 58 PSIG, the eductor audibly took suction, and began pumping HF Acid. The pressure on the acid storage drum was raised to 70 PSIG during the duration of the educting.

At 10:30 A.M. the eductor began pumping the HF acid. The original level in the vessel was noted at 2.3 feet.

At 1:30 P.M. the eductor was isolated from the HF acid storage drum. The level in the vessel was noted at 0.8 feet. Over a period of 3.0 hours 1.5 feet of HF Acid were pumped from the acid storage drum to the unit. This is an average rate of approximately 16 GPM. All of the acid lines were then flushed clean, isorecycle rate was increased by 5,000 BPD back to normal rates, and the eductor was isolated to complete the acid addition procedure.

In general a positive response was received on the system from the operation personnel. The following comments and suggestions were made:

1. In reviewing the performance of the educting system it was noted that it was difficult to balance the isorecycle flows in the unit, since no direct flow measurement is available on the isobutane used as the motive force to the eductor. It is recommended that a DCS mounted flow meter be installed on the motive isorecycle to the eductor to aid in prevention of upsets when lining the eductor out, and also to help in making sure that adequate motive fluid flow is going through the eductor to obtain proper performance.
2. It was also noted that the Acid Relief neutralizer system took a fairly good hit during the educting operation. The effects of this can be minimized by raising the set pressure on the pressure controller on the acid storage drum. This will limit the amount of venting from the storage drum. The pressure controller can be set to a maximum of 135 PSIG. The acid storage drum pressure will then be controlled with a pressure regulator on the incoming fuel gas. This pressure is to be set at 80 PSIG. These changes can be made with revisions to the operating procedures, and no equipment modifications.
3. It was also noted that an unexpected benefit of the eductor occurred. Previously, HF acid addition resulted in a large volume of fresh acid being transferred into the mixer settler. This fresh acid raised acid purity and resulted in an alkylate production spike, which caused a minor unit upset, until the fresh acid was diluted and the alkylate production returned to normal. The new eductor added the fresh acid slow enough that it did not cause the alkylate spike to occur.
4. It was noted that the unit provided an average flow of 16 GPM was drawn from the eductor. The eductor was designed to provide a flow rate of 25 GPM. Because of lack of information on the motive flow rate, and lack of a PI tag on the acid storage drum level to infer flow rate from the eductor, the flow rate the eductor was pumping at can not be accurately determined and no conclusions can be made as to the eductor's performance. The eductor rate will be checked against design after the addition of the motive fluid flow meter is completed.

Typical charge rates for some streams in an HF alkylation unit are shown in Table I.

| DESCRIPTION Component | ISOBUT. FEED | DRY FEED TO REACTOR | DRY SATUR. FEED | ALKY PRODUCT | IC RECYCLE |
|---|---|---|---|---|---|
| BP SD | 156 | 5.244 | 6.656 | 7,996 | 67,522 |
| GP GR. 60° F. (mw) | 0.562 | 0.557 | 0.573 | 0.697 | 0.561 |
| LB/HR TOTAL COMPONENTS, MPH | 1,295 | 66,969 | 55,576 | 31,176 | 554,891 |
| $C_2$ & LIGHTER | | 3.2 | | | |
| $C_3=$ | | 375.5 | | | |
| $C_3$ | 0.3 | 262.0 | 22.3 | | 1453.2 |
| $iC_4$ | 21.1 | 262.5 | 502.5 | 0.8 | 7709.5 |
| $C_4=$ | | 342.5 | | | |
| $nC_4$ | 0.7 | 85.1 | 415.9 | 52.3 | 513.2 |
| C5's | 0.2 | 10.4 | 16.5 | 36.6 | 25.2 |
| $C_6+$ | | | | 691.8 | 52.0 |
| ALKYLATE | | | | | |
| HF | | | | 235.4 | |
| H2O | | | | | |
| TOTAL | 22.3 | 1325.3 | 957.5 | 751.5 | 3753.1 |

For such a plant, when makeup HF acid addition is practiced, the flow rate of makeup HF acid is 25 gpm, the amount of isobutane recycle is 228 gpm, producing 253 gpm of HF/isobutane.

When restoring acid inventory, the recycle isobutane flow is much larger, 600 gpm, and the recycle isobutane pump discharge pressure is increased from 325 to 345 psig. This larger volume and increased pressure of isobutane are sufficient to educt 150 gpm of HF from the storage tank into the plant.

Changes and modifications in the specifically described embodiments can be carried out without departing from the scope of the invention which is intended to be limited only by the scope of the appended claims.

What is claimed is:

1. A HF alkylation process comprising:
   (a) mixing liquid HF acid, a fresh isobutane feed stream, a recycle isobutane stream and a fresh olefin feed stream to form a liquid mixture;
   (b) alkylating said olefins in said mixture with isobutane in an HF alkylation reactor operating at HF alkylation conditions including a pressure sufficiently high to maintain said isobutane in the liquid phase in at least a portion of said reactor, to form a liquid mixture comprising isoparafinnic alkylate produced in the course of said alkylation reaction, alkyl fluorides, and HF contaminated with a minor amount of acid soluble oil (ASO) produced during said alkylation reaction;
   (c) separating said mixture into an alkylate product rich phase, a recycle liquid HF acid phase contaminated with ASO, and an isobutane recycle phase,
   (d) regenerating, at least periodically, a portion of said recycle liquid HF acid in an acid regenerator to remove ASO therefrom and produce an ASO-rich stream containing a minor portion of acid or alkyl fluorides and a regenerated HF acid stream which is recycled to said alkylation reactor;
   (e) consuming, at least a portion of said liquid HF acid by at least one of mechanical loss, formation of alkyl fluorides which remain in a liquid alkylate product phase, or losses associated with a regeneration step;
   (f) storing fresh liquid HF acid in an HF acid storage vessel at liquid HF storage conditions sufficient to maintain said acid in a liquid phase and at a superatmospheric pressure which is below the pressure of said alkylation reactor; and
   (g) educting, at least periodically, liquid HF acid from said storage vessel to said HF alkylation process by educting liquid HF acid from said storage vessel using an eductor and as a motive fluid a liquid phase hydrocarbon feed or product stream associated with said alkylation process.

2. The process of claim 1 wherein said motive fluid is alkylate.

3. The process of claim 1 wherein said motive fluid is isobutane.

4. The process of claim 1 wherein said HF alkylation reaction n conditions include a pressure above 200 psig and said liquid HF acid storage conditions include a pressure below 200 psig.

5. The process of claim 1 wherein said motive fluid is a portion of said isobutane recycle stream.

6. The process of claim 5 wherein said alkylation conditions include an isobutane:olefin mole ratio and wherein said ratio is maintained by splitting isobutane recycle into at least two streams, one to said HF alkylation reactor and one to serve as said motive fluid.

7. The process of claim 6 wherein a flow indication means is provided on at least one member of the group of said recycle isobutane streams and said motive fluid.

8. The process of claim 7 wherein flow indication and control means on both said recycle isobutane stream and said motive fluid stream are used to maintain a constant isobutane:olefin mole ratio in at least that portion of said process downstream of a point used to add fresh HF acid from said HF acid storage vessel.

9. The process of claim 1 wherein said motive fluid is all or a portion of said fresh isobutane stream.

10. The process of claim 1 wherein at least two eductors in parallel are used.

11. A method of periodically adding fresh or makeup HF acid to an HF alkylation process operating at a pressure above 200 psig from a liquid HF acid storage tank operating at a pressure below 200 psig and wherein said pressure differential between said process and said storage tank is sufficient to preclude use of a recycle isobutane stream produced in said alkylation process to educt liquid HF from said storage tank into said alkylation process comprising:

(a) temporarily increasing the pressure in said liquid HF storage tank above said normal storage tank operating pressure;

(b) diverting a portion of a recycle isobutane stream from said plant to use as a motive fluid in an eductor fluidly connected with said liquid HF storage tank; and said alkylation reaction; and (c) discharging from said eductor a stream comprising isobutane motive fluid and educted liquid HF acid into a portion of said HF alkylation process.

12. A method of restoring an inventory of HF acid to an HF alkylation process after a shutdown of the HF alkylation plant to permit using said inventory of HF acid to alkylate a fresh olefin stream with a stream comprising recycle isobutane produced in one or more fractionators to produce alkylate comprising:

(a) restoring isobutane recycle by adding isobutane and a startup alkylate stream to said alkylation unit and-fractionating same in said one or more fractionators to produce an isobutane recycle stream and a startup alkylate stream with a reduced isobutane content to establish temperatures and operating conditions in said one or more fractionators and startup pressures in said process;

(b) educting a stored HF inventory from an HF inventory storage tank operating at HF storage conditions including a pressure less than said startup pressure in said process into said HF alkylation plant using a recycle isobutane stream produced by said one or more fractionators to produce an HF alkylation plant with isobutane recycle established and an inventory of HF acid in the plant.

13. The process of claim 12 wherein said HF inventory storage tank operates at 50 to 150 psig and acid is educted into a part of the process with a startup pressure at least 50 psi higher than said storage tank.

* * * * *